United States Patent [19]

Guiseppi-Elie

[11] Patent Number: 5,102,798
[45] Date of Patent: Apr. 7, 1992

[54] SURFACE FUNCTIONALIZED LANGMUIR-BLODGETT FILMS FOR IMMOBILIZATION OF ACTIVE MOIETIES

[75] Inventor: Anthony Guiseppi-Elie, Yardley, Pa.

[73] Assignee: Allage Associates, Yardley, Pa.

[21] Appl. No.: 241,607

[22] Filed: Sep. 8, 1988

[51] Int. Cl.$^5$ .................. C12N 11/02; C12N 11/08; G01N 33/544; G01N 33/545
[52] U.S. Cl. .................. 435/177; 264/165; 435/180; 435/181; 436/528; 436/531; 436/532; 530/812; 530/815; 530/816
[58] Field of Search .............. 435/174, 177, 180, 181; 436/528, 531, 532; 530/812, 815, 816; 264/165

[56] References Cited

U.S. PATENT DOCUMENTS

| | | | |
|---|---|---|---|
| 4,451,619 | 5/1984 | Heilmann et al. | 525/384 X |
| 4,548,873 | 10/1985 | Yamamoto et al. | 428/694 X |
| 4,554,076 | 11/1985 | Speaker | 210/500.28 X |
| 4,562,157 | 12/1985 | Lowe et al. | 435/186 X |
| 4,820,649 | 4/1989 | Kamaguchi et al. | 436/525 X |
| 4,886,685 | 12/1989 | Wegner et al. | 427/435 X |
| 4,923,288 | 5/1990 | Allen et al. | 350/355 |

OTHER PUBLICATIONS

Guiseppi-Elie et al., Journal of Polymer Science, vol. 23, 1985, pp. 2601-2613.

Primary Examiner—David M. Naff
Attorney, Agent, or Firm—Synnestvedt & Lechner

[57] ABSTRACT

Langmuir-Blodgett films having hydrophobic surfaces are chemically modified to convert the hydrophobic surfaces to hydrophilic surfaces for immobilization of active moieties having bioactive, immunoactive, thermoactive, electroactive, optoactive or redoxactive properties. Langmuir-Blodgett films having a hydrophobic surface of omega unsaturated covalent bonds are formed from an amphiphilic, bifunctional surface active material having a hydrophobic tail group bearing an omega terminus of double or triple bonded unsaturation. The amphiphilic material may be fatty acids, phospholipids or porphyrins, and is preferably omega-tricosenoylamide or omega-tricosenoic acid. Chemical modification is carried out by exposing the hydrophobic surface to a reagent such as alkaline or acidic potassium permanganate, potassium dichromate or osmium tetroxide which oxidizes the omega unsaturated covalent bonds to provide hydrophilic groups such as hydroxyl or carboxylic acid groups. These groups make the film surface hydrophilic and function as sites for attachment of the active moieties.

48 Claims, 8 Drawing Sheets

FIG. 1

"Z"-Type L-B Film
FIG. 2c

"X"-Type L-B Film
FIG. 2b

"Y"-Type L-B Film
FIG. 2a

HYDROPHOBIC SURFACE

HO-CO-(CH$_2$)$_{20}$-CH=CH$_2$  H$_2$C=CH-(CH$_2$)$_{20}$-CO-OH  HO-CO-(CH$_2$)$_{20}$-CH=CH$_2$ $\downarrow$ 0.01M KMnO$_4$ (aq), pH 9, 4°C

HO-CO-(CH$_2$)$_{20}$-CH=CH$_2$  H$_2$C=CH-(CH$_2$)$_{20}$-CO-OH  HO-CO-(CH$_2$)$_{20}$-CH(OH)-CH$_2$(OH)

cis-1,2-diol

HYDROPHILIC SURFACE

FIG. 3

HYDROPHOBIC SURFACE 0.04% OsO$_4$, 30sec, 20°C 0.01M Na$_2$SO$_3$, 1.0 min., 20°C.

HYDROPHILIC SURFACE

SURFACE FUNCTIONALIZED LANGMUIR-BLODGETT FILMS FOR IMMOBILIZATION OF ACTIVE MOIETIES

BACKGROUND OF THE INVENTION

Surface structure and composition play a significant role in determining the physicochemical properties of solid materials. Of particular interest are fundamental material properties such as wetting, adsorption, adhesion, friction, electrostatic charging, and biocompatability. The ability to alter the chemistry and structure of surfaces is accordingly of great technological significance.

One approach to the chemical modification of solid surfaces is via the deposition of Langmuir-Blodgett films as disclosed in the following literature: K. B. Blodgett, *J. Am. Chem. Soc.*, 56:495 (1934); K. B. Blodgett, *J. Am. Chem. Soc.*, 57:1007 (1935); K. B. Blodgett and I. Langmuir, *Phys. Rev.*, 51:964 (1937); G. L. Gaines, Jr., *Thin Solid Films*, 68:1 (1980); G. G. Roberts, *Contemp. Phys*, 25 (2):109 (1984); and U.S. Pat. No. 4,554,076, of Speaker.

Langmuir-Blodgett (hereinafter referred to alternatively as "L-B") films are ultra-thin organic films of molecular dimensions fabricated from the sequential transfer of monomolecular layers of surface-active molecules previously cast onto a liquid surface. The floating precursor films, (called Langmuir films or spread monolayers), comprise surface active molecules such as long chain fatty acids, lipids, phospholipids, proteins, polymers, porphyrins, and the like, with ionizable or non-ionizable polar head groups and lipophilic tail segments. Such materials, having a combination of both hydrophilic and hydrophobic properties are commonly referred tc as amphiphilic materials.

In the formation of Langmuir-Blodgett thin films, the surface active material is first prepared as a dilute solution in a suitable organic carrier solvent such as heptane or chloroform. The solution is then applied to a surface of a Langmuir trough so as to spread out mono-molecularly thereupon. This monolayer film is subsequently compressed to yield a pseudo-solid film. In one method, compression is achieved by moving the subphase beneath the film as described in Japanese Patent 60-193532. Alternatively, compression can be achieved by moving the gaseous phase above the film or by moving a solid barrier at the film periphery.

A typical Langmuir trough comprises a means for containing the liquid subphase. A working area is defined by a barrier (for example, a PTFE-coated glass fiber) which defines the area to be occupied by the monolayer. This barrier can be moved using a means such as a low-geared electric motor. By moving the barrier to increase or decrease the area defined therein, it is possible to maintain a constant barrier layer pressure as the volume of the monolayer material is decreased via deposition onto the substrate.

The barrier motor can be coupled to a sensitive electronic balance which continuously monitors, via means such as a sensing plate, the surface pressure of the monolayer. Using feedback monitoring, the monolayer pressure can be maintained at a predetermined value.

The physical dimensions of the Langmuir trough are largely arbitrary, being governed only by the size of the substrate upon which the film is to be deposited. Strict cleanliness conditions are considered necessary to produce films of uniform quality. As such, Langmuir-Blodgett film deposition systems are usually maintained in controlled environments such as within glove boxes, laminar flow hoods, or in clean-rooms such as those used for pharmaceutical or microelectronic fabrication.

The solid substrate onto which the film is to be deposited is made to cut the surface of the monolayer-bearing subphase, usually vertically or at an angle, by lowering the solid substrate into the liquid subphase through the monolayer. In so doing, the compressed monolayer film is transferred to the solid substrate. By reciprocating the solid substrate through the surface of the subphase, several monolayers can accordingly be built-up onto the solid support. This technique is commonly referred to as the Langmuir-Blodgett Technique and the films formed thereby are commonly referred to as Langmuir-Blodgett films.

The deposition of a Langmuir-Blodgett (L-B) film occurs in such a manner as to result in the formation of one of three basic types of organized structure. These structures are commonly referred to as x-, y-, and z-type films, the most common being the y-type. In a y-type film, the immersion of a hydrophobic substrate into the monolayer-containing subphase results in a strong hydrophobic association between the hydrophobic surface of the substrate and hydrophobic terminals of amphiphilic monolayer entities. The hydrophobic attachment results in the exposure of the hydrophilic terminals of the monolayer entities on the immersed film. When the film is raised through the monolayer, however, the exposed hydrophilic terminals associate with hydrophilic terminals of the monolayer entities to result in a film having an exposed hydrophobic surface. As the film is gradually built-up by repeated traversal of the monolayer surface, the exposed film surface upon removel from the subphase tends to exhibit continued hydrophobic-properties.

In less common configurations, such as in the x-type structure, a weak hydrophobic interaction between the substrate and the hydrophobic terminals of monolayer entities first occurs. Subsequent monolayer traversals either into or out of the subphase liquid result in a weak hydrophobic-hydrophilic interaction between the hydrophilic head groups of one film layer with the hydrophobic tail groups of a subsequently deposited film layer. Similarly, in the z-type film structure, an initial film layer is deposited through a weak association between the hydrophobic surface and hydrophilic terminals of monolayer entities. This results in a surface having exposed hydrophobic terminals. Subsequent layers are deposited by similar hydrophobic-hydrophilic associations resulting in a built-up film having a hydrophobic surface characteristic. Thus, the z-type structure, like the y-type structure, provides a film having hydrophobic surface properties. In contrast, x-type films, which are deposited by interaction of hydrophobic terminals with the underlying film layer, have hydrophilic surface properties.

For many years, these films were generally regarded as little more than an academic curiosity (G. L. Gaines, *Insoluable Monomers at Liquid Gas Interface*, Interscience Publishers, N.Y. (1966)). In recent times, however, it has become apparent that these films can have great utility in areas as diverse as electronics (P. S. Vincent and G. G. Roberts, *Thin Solid Films*, 68:135 (1980)); tribology (U.S. Pat. No. 4,548,873 of Yamamoto et. al.); molecular electronic devices (G. G. Roberts, *Sensors and Actuators*, 4:131 (1983) and G. G. Roberts, *Adv.*

Phys., 34 (4):475 (1985)); molecular signal generation and processing (H. Kuhn, *Naturwiss,* 54:429 (1967) and H. Kuhn, *Photochem.* 10: 111 (1979)); optical devices (B. Liedberg et. al., *Sensors and Actuators,* 4:299 (1983)); and electro-optics (D. B. Neal et. al., *Electronics Letters,* 22 (9):460 (1986) and G. M. Carter et. al., *Optical Engineering,* 24 (4); 609 (1985)).

In many technological applications of L-B films, there is a need to achieve a topologically uniform, ultra-thin organic overlayer of controlled and uniform surface chemistry. However, the fabrication techniques associated with L-B films often yielded hydrophobic surfaces and these hydrophobic surfaces were generally chargeless and unreactive. As such, these films to date have generally been limited to applications in which hydrophobic surface characteristics are desirable.

SUMMARY OF THE INVENTION

This invention relates to new organic thin films formed by the surface chemical modification of built-up L-B films and also to the subsequent derivatization or functionalization of chemically modified L-B film surfaces.

The L-B films of this invention are formed from amphiphilic, surface active molecules which have both ionizable and non-ionizable head groups. Such materials generally bear an omega-terminus of double or triple bonded unsaturation. Mixtures of these molecules with fully saturated counterparts can also be used. Suitable amphiphilic materials include fatty acids, phospholipids, porphyrins and their derivatives. Preferred amphiphilic materials include omega-tricosenoylamide, omega-tricosenoic acid, arachidic acid, stearic acid, heptadecanoic acid, hexadeconic acid, phthalocyanine, merocyanine, phosphatidylcholine, bis-[12-(methacryloyloxy)dodecanoyl]-L-phosphatidycholine and derivatives thereof. A post-fabrication reaction is employed in which the surface of the built-up L-B film is exposed to chemical agents which act to convert high surface unsaturation into reactive, functional groups such as hydroxyls, halides, acids, amines, amides, alcohols, sulphonates, esters, acrylates, methacrylates and the like. Preferred halides include chloride, bromide and iodide. Carboxylic acids are a preferred variety of acid. These added functional groups can render the film hydrophilic and reactive and also serve as sites for the specific attachment of active moieties to the surface of the L-B film, thereby forming a supra-macromolecular complex. Such moieties can, for example, impart bioactive, immunoactive, electroactive, optoactive, thermoactive or redoxactive properties to the film surface. Preferred bioactive moieties include antigens, antibodies, allergens, proteins (both simple and complex), enzymes, cofactors, RNA, DNA, hormones, enzyme conjugates, enzyme inhibitors and enzyme substrates. Preferred immunoactive moieties include monoclonal and polyclonal antibodies and antigens. Preferred electroactive moieties include electroactive cofactors and ferrocenecarboxylate. Diacetylenes are the preferred optoactive moieties.

The surface chemical modification of an L-B film and the subsequent surface immobilization to the hydrophilic organic moieties to achieve a supramacromolecular complex can be carried out after fabrication of the built-up L-B film onto any of a wide variety of solid substrates. These solid substrates include, but are not limited to glass, polymers, ceramics, semiconductors and the like.

In a broad sense, the present invention involves a chemical reaction on the surface of an L-B film monolayer which alters the surface reactivity and hydrophobic character and renders the surface hydrophilic. This allows for the deposition of subsequent monolayers through hydrophilic-hydrophilic interactions. Alternatively the surface alteration allows covalent attachment of active moieties through the enhanced reactivity that has been imparted to the film surface.

DESCRIPTION OF THE INVENTION

The present invention pertains to a method for producing L-B films which results in films which are hydrophilic at the surface, reactive with other molecules (to thereby yield surface derivatized complex structures), and chemically homogenous at the surface.

Moreover, the invention pertains to the introduction, via adsorption or through specific immobilization, of various other molecules which are different in function and purpose to the underlying substrate layer. These molecules, termed overlayer molecules, can confer to the L-B film the properties of the new overlayer and can also interact with the underlayer so as to produce some new overall effect or material property. Such complex, composite, layered structures are referred to as supra-macromolecular assemblies.

Figure 1:
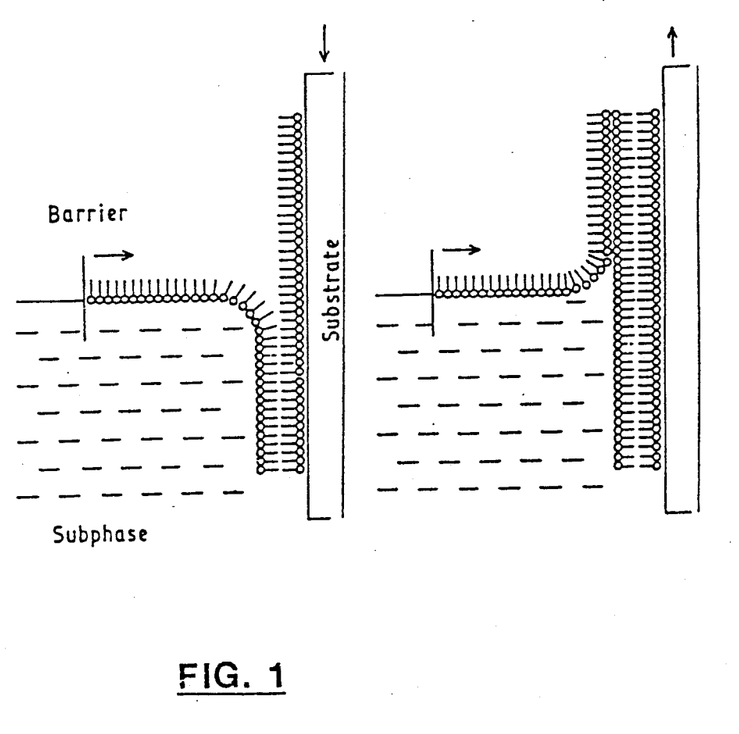
FIG. 1 is a representation of the deposition process for the fabrication of Langmuir-Blodgett films.

FIG. 1 is a representation of a deposition process for the fabrication of a typical, y-type, Langmuir-Blodgett film. In this Figure, a substrate having hydrophobic surface properties is immersed into a liquid subphase through a monolayer of amphiphilic material. This results in an interaction between the substrate and hydrophobic terminals of the monolayer material. Upon withdrawal of the substrate, however, interaction between hydrophilic terminals of the monolayer material and the exposed, hydrophilic surface of the film result in a subsequent film deposition in which the exposed surface of the film is hydrophobic. Examples of this type of interaction include, but are not limited to the association between fatty acids and their derivatives with substrate surfaces.

Another amphiphilic material which forms L-B films is omega-tricosenoic acid. This molecule, with the structural formula, $CH_2=CH-(CH_2)_{20}-COOH$, has a hydrophobic group on one end, (the hydrocarbon chain), and a hydrophilic group at the other end, (the carboxylic acid). Consequently, the carboxylic acid group will associate with a hydrophilic surface, thereby resulting in a monolayer with the polymerizable group, such as a vinyl, on the surface. When an L-B film is fabricated according to this method, the surface of the resulting built-up film is generally hydrophobic.

A typical process for the deposition of an L-B film formed from a fatty acid or fatty acid derivative is as follows. The environmental temperature is generally between about 20° and 25° C., the pH of the subphase is about 7.0, the compression rate of the monolayer is about 2.0 cm/min, and the dipping rate of the substrate is about 2 mm/min. It must be pointed out that while the above conditions are preferred, they are not intended to limit the invention as such.

A casting solvent is used to form a dilute (approximately $10^{-3}M$) solution of the surface active, film forming molecule. Such solvents are generally pure or mixed organic solvents which can readily dissolve the surfactant, are substantially insoluble in water, are volatile, and have a positive spreading coefficient on water. Preferred solvents include heptane, hexane and chloroform. The solution of surface active molecules in the solvent is applied to the working surface of the subphase to produce a surface having about one surface active molecule per 100 $A^2$. This solution is generally applied to the surface in volumes of between about 30 to about 50 ul via a micropipette.

The volatile organic solvent is allowed to evaporate and the film is then compressed to its deposition pressure. This pressure typically corresponds to a value in the pseudo-solid state as determined from the monolayer isotherm. A typical deposition pressure value is about 30 mN/m. The film compression rates are typically about 2 cm/min and deposition rates are typically about 2 mm/min. It should be pointed out, however, that deposition rates of up to about 5 cm/sec are possible.

The subphase pH is typically neutral, however, it can be adjusted if desired. For example, buffers and salts can be added if the subphase pH is to be altered.

Figure 2A:
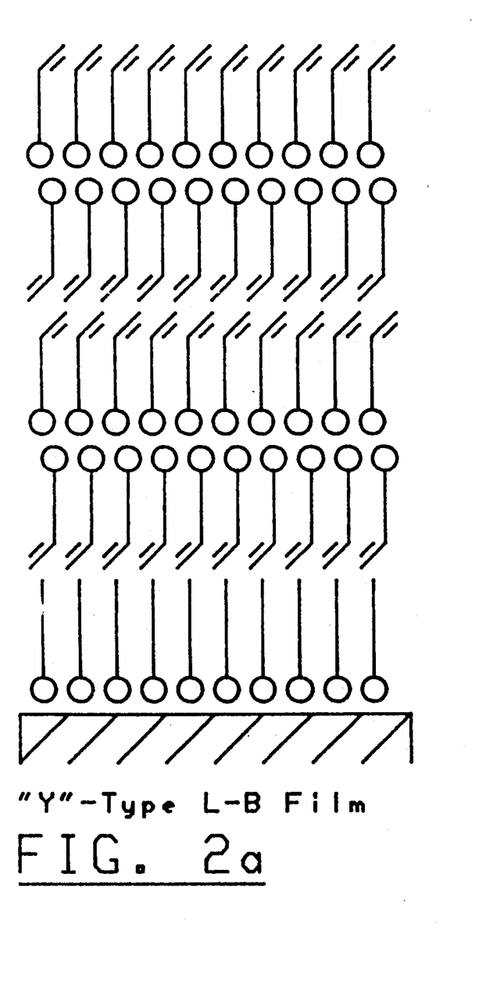
FIG. 2 is a representation of three types of structural orientations of the surface active molecules which can result from the Langmuir-Blodgett film deposition process.

FIG. 2a illustrates a y-type multi-layer structure that can result from the deposition process presented in FIG. 1. It can be seen that this process, which is the most common method for preparing L-B films, results in a hydrophobic surface.

Figure 2B:
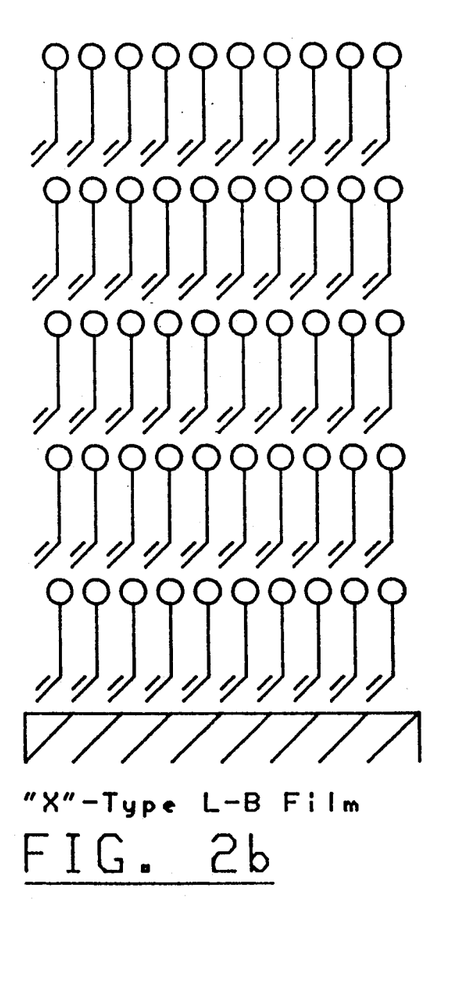

FIG. 2b illustrates the less common x-type of film structure wherein the first monolayer is deposited upon a substrate via a hydrophobic-hydrophobic interaction. The association of an olefin group with the surface of the substrate can be clearly seen. The deposition of subsequent monolayers, however, is achieved through the use of weak hydrophilic-hydrophobic interactions. The resulting film surface exhibits hydrophilic properties. This type of deposition, however, is quite rare because relatively few hydrophilic moieties are capable of both hydrophilic and hydrophobic associations. Of the materials which can be used for this type of deposition, carboxylic esters, particularly long chain ester moieties which have both hydrocarbon chains for hydrophobic interaction and ester carbonyls having sufficient polarity for limited hydrophilic association are preferred.

Figure 2C:
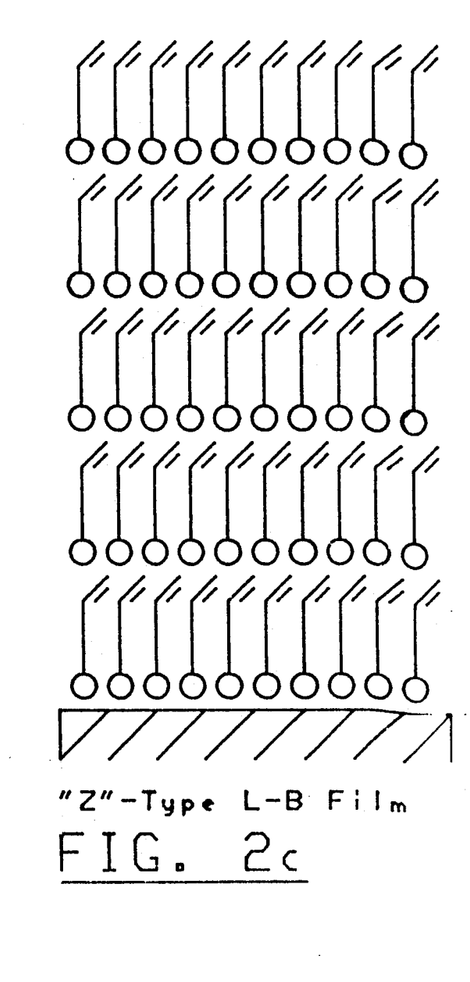

The z-type structure presented in FIG. 2c is an analog to the structure of FIG. 2b. In FIG. 2c, the first monolayer that is deposited on a given substrate utilizes a hydrophilic-hydrophilic association. The subsequent monolayers are then associated through a similar but weak hydrophobic-hydrophilic interaction with the resulting surface of the film indicating hydrophobic character. However, as with the x-type structure, the z-type structure is relatively uncommon.

The y-type film structure depicted in FIG. 2a is the most common L-B film. In such films, the final surface is completely hydrophobic and is not capable of further direct association with hydrophilic reagents.

Furthermore, to date, very few materials have been found suitable for making L-B films since these materials must combine properties which include organic solubility, stability at the surface of the subphase, suitable orientation and compaction, shear resistance and cohesion. Adhesion between the first monolayer and the substrate and between subsequent monolayers is often of crucial importance (G. G. Roberts and M. C. Petty, *Encyclopedia of Material Science and Engineering*, 4:2494 (1986)). Consequently, if a hydrophilic surface requires a hydrophilic association of the first monolayer, the resulting hydrophobic surface limits the ability of the L-B film to immobilize reagents which require hydrophilic interactions.

The reaction of hydrophobic functional groups (such as those having double bonds and triple bonds) with aqueous oxidants such as potassium permanganate, potassium dichromate and osmium tetroxide has been shown to result in the introduction of polar functionalities in bulk chemical processes (see A. Guiseppi-Elie and G. E. Wnek, *J. Polym Sci., Polym. Chem. Ed.*, 23:2601 (1985); J. March, *Advanced Organic Chemistry*, 2nd Ed., McGraw-Hill, New York, 748-749 (1977)). However, until the present invention, the application of this chemistry to the surface of a built-up Langmuir-Blodgett film has not been reported or considered practical. Other reactive surface functionalities such as amines and sulphonates can be similarly provided to the film surface. This allows the introduction to the film surface, via absorption or through specific immobilization, of various other molecules which are different in function from the underlying substrate layer. These overlayer molecules can confer to the L-B film the properties of a new outerlayer and can also interact with the underlayer so as to produce a new overall effect or material property. Such complex, composite, layered structures are referred to herein as supramacromolecular complexes. Examples of such supramacromolecular complexes include redox active, bioactive, immunoactive, thermoactive, optoactive and electrically active moieties immobilized in the surface of chemically modified L-B films.

Figure 3:
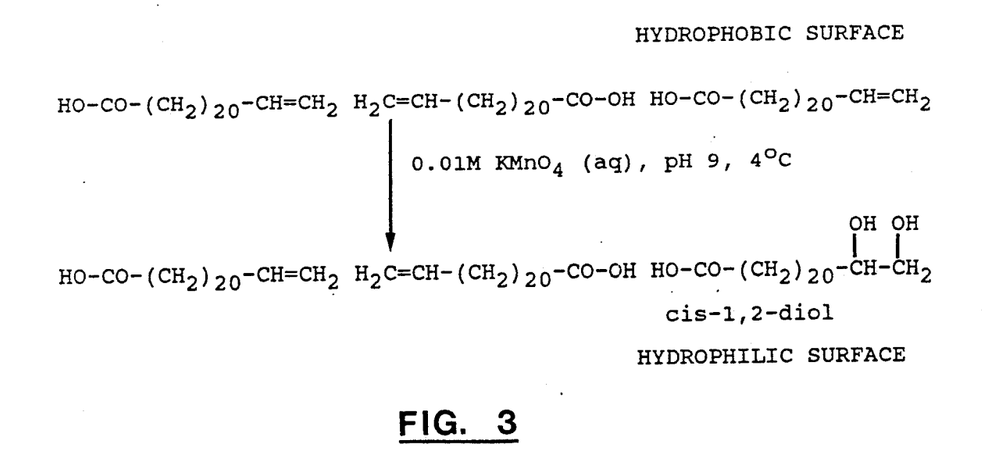
FIG. 3 illustrates the chemistry of a surface modification reaction using aqueous, alkaline, potassium permanganate ($KMnO_4$) oxidation.

FIG. 3 presents the chemistry for the modification of an L-B film having a hydrophobic surface of omega-tricosenoic acid through the use of the aqueous reagent, potassium permanganate. The reaction is preferably carried out at a pH of about 9 and at a temperature of about 4° C. As can be seen, the hydrophobic olefin group is converted to hydrophilic surface hydroxyls. These hydroxyl groups allow for future interaction with a hydrophilic reagent.

Figure 4:
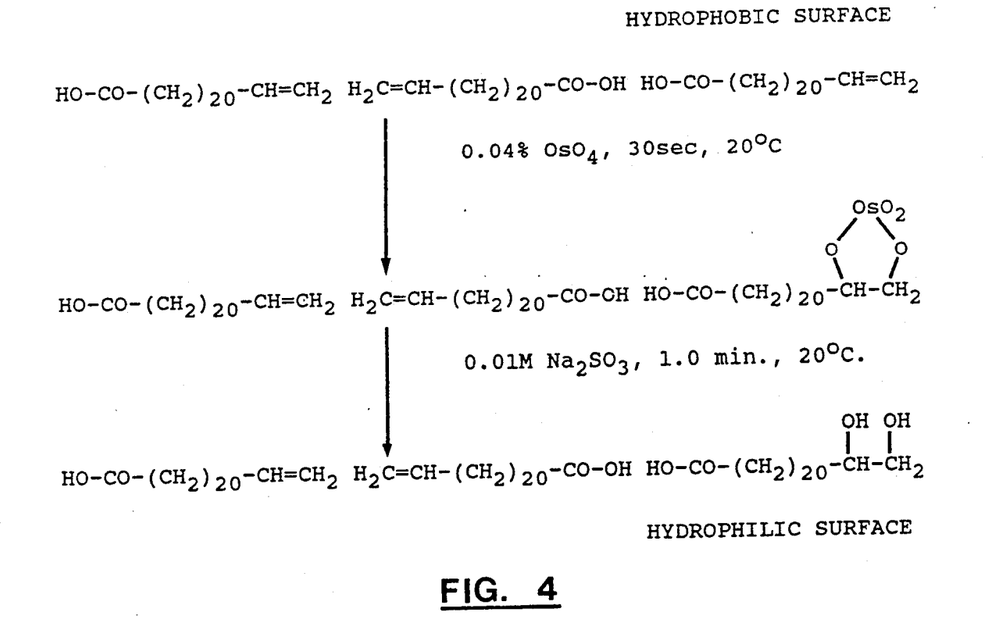
FIG. 4 illustrates the chemistry of a surface chemical modification reaction using osmium tetroxide ($OsO_4$)

FIG. 4 illustrates another embodiment in which a hydrophobic olefin group is converted to hydrophilic surface hydroxyls through the use of the aqueous reagent, osmium tetroxide. In this reaction, a 0.02% aqueous solution of OsO₄ is contacted with the hydrophobic film surface for about 30 sec. at a temperature of about 20° C. Subsequently, an aqueous solution of about 0.01M Na₂SO₃ is contacted with the film surface for about 1.0 min. at a temperature of about 20° C. The resulting surface contains a hydrophilic, hydroxyl functionality.

Figure 5:
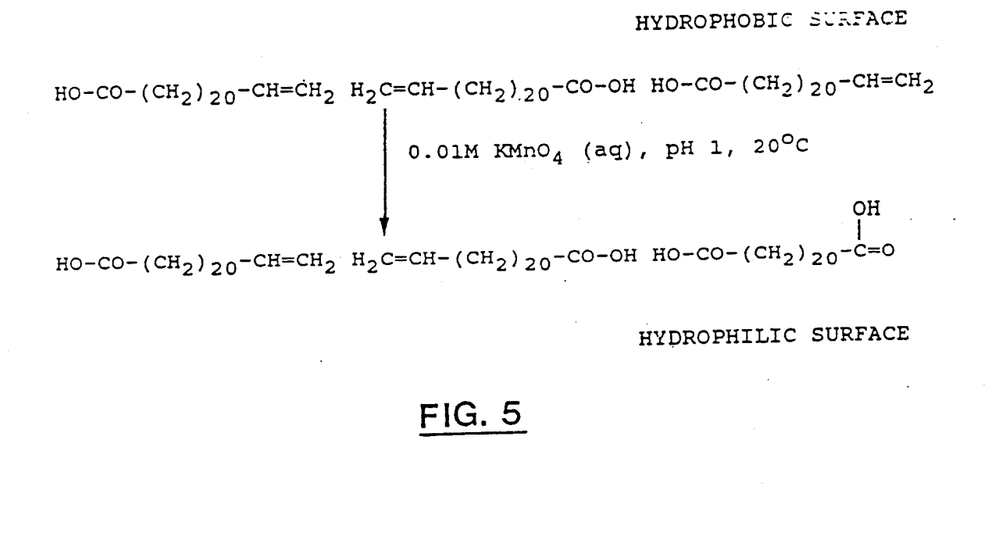
FIG. 5 illustrates the chemistry of a surface chemical modification reaction using aqueous, acidic, potassium permanganate ($KMnO_4$) oxidation.

FIG. 5 illustrates yet another embodiment in which the hydrophobic olefin group of the L-B surface is converted to a hydrophilic surface having carboxyl functionality through the use of the aqueous reagent, potassium permanganate. This reaction is carried out using preferably about 0.01M KMnO₄ at a pH of about 1.0 and at a temperature of about 20° C.

Figure 6A:
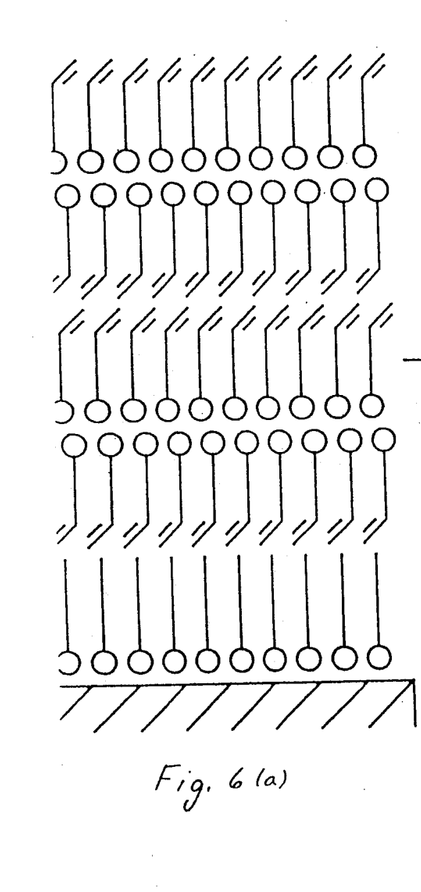
FIG. 6 illustrates the formation of a supra-macromolecular complex by the subsequent deposition of a second L-B monolayer following surface chemical modification.
Figure 6B:
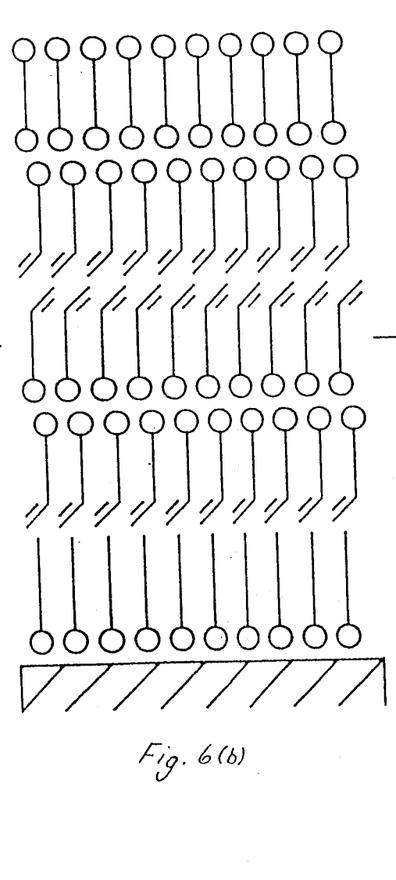
Figure 6C:
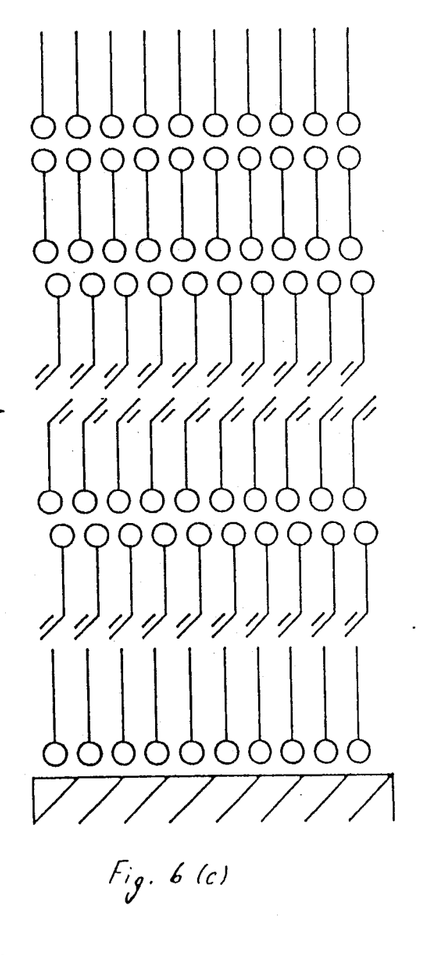

FIG. 6 illustrates the formation of a supra-macromolecular complex by the deposition of a subsequent L-B film onto a chemically modified L-B film surface. In FIG. 6(a), a typical y-type L-B film is schematically depicted. In FIG. 6(b), the surface layer of the L-B film has been chemically modified to convert the original hydrophobic functionality to a hydrophilic functionality. This results in a monolayer having a hydrophilic functionality at each terminal end. In FIG. 6(c), the hydrophilic nature of the chemically modified surface has been utilized to immobilize a subsequent L-B film upon the chemically modified surface.

Figure 7:
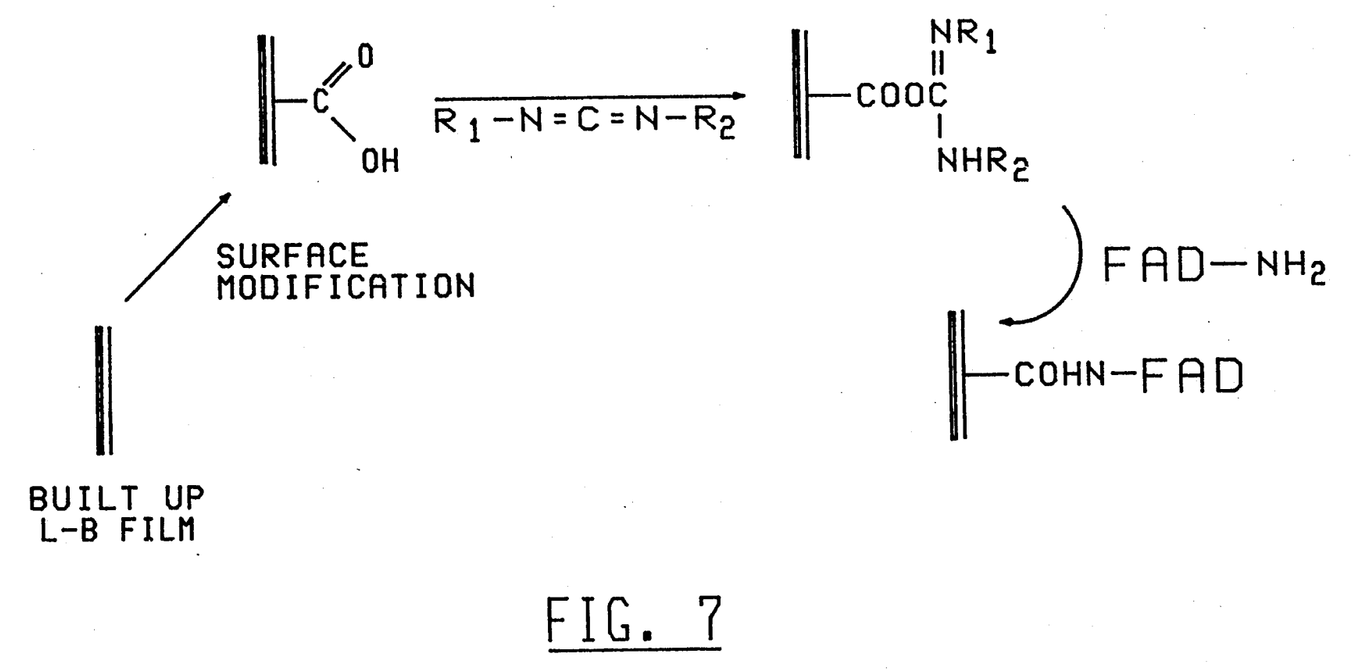
FIG. 7 illustrates the formation of a supra-macromolecular complex from the specific immobilization of the enzyme co-factor FAD to the surface of a chemically modified built-up L-B film.

FIG. 7 illustrates the chemical process for the immobilization of the enzyme cofactor flavin adenine dinucleotide (FAD) upon an L-B film. In FIG. 7, a built-up L-B film is provided with a carboxyl (—COOH) functionality. The —COOH groups are then reacted with a carbodiimide of the general formula $R_1$—N=C=N—$R_2$, wherein $R_1$ and $R_2$ can be either the same or different and are materials such as hydrogen, halogens and the like. In the preferred embodiment, the carbodiimide has the formula, H—N=C=N—H. Once the surface has been reacted with the carbodiimide, it is exposed to the cofactor FAD. This results in a supramacromolecular surface in which FAD is immobilized upon a chemically modified L-B film.

Figure 8:
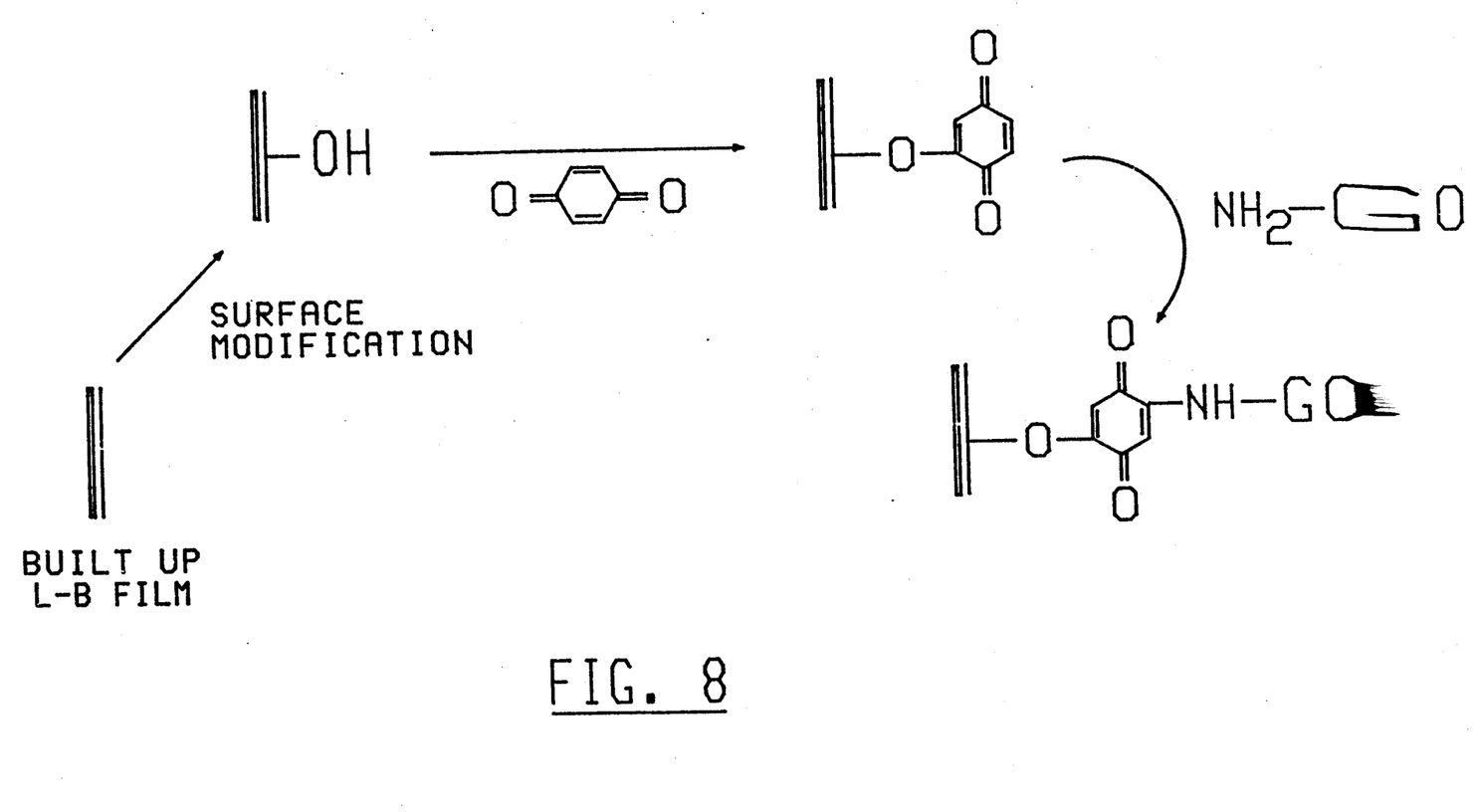
FIG. 8 illustrates the formation of a supra-macromolecular complex from the specific immobilization of the enzyme glucose oxidase to the surface of a chemically modified, built-up L-B film.

FIG. 8 illustrates the chemical process for the immobilization of the enzyme glucose oxidase (GO) upon an L-B film. In FIG. 8, a built-up L-B film is provided with a hydroxyl (—OH) functionality. The —OH groups are then reacted with benzoquinone. Subsequently, the surface is exposed to glucose oxidase. This results in a supra-macromolecular surface in which GO is immobilized upon a chemically modified L-B film.

The invention will now be more particularly pointed out in the following Examples.

EXAMPLE 1

Omega-Terminus Tricosenoylamide L-B Films Fabricated by Deposition on a Joyce Lobel Langmuir Trough A dilute solution ($10e^{-3}$M) of omega-tricosenoylamide was prepared by dissolution in chloroform at room temperature. The solution was spread onto the water surface of a Joyce Lobel Langmuir Trough with the subphase temperature maintained at about 20° C. The solvent was allowed to evaporate for 1 to 5 minutes before the film was compressed at 2 cm per min. to a deposition film pressure of 30 mN m$^{-1}$. Previously cleaned and conditioned, chromium plated, soda lime glass slides, each 3"×3" (EMC Micromask LRG 306), were then dipped repeatedly through the interface for the total deposition of 30 built-up monomolecular layers. The resulting film was deposited as an approximately 1 cm band across the 3" wide plate.

EXAMPLE 2

Omega-Terminus Tricosenoylamide L-B Films Fabricated by Deposition on a Molecular Electronics Corporation Monofab II Trough In this example, the L-B film is prepared according to the general description provided for above in Example 1 except that the film is fabricated by deposition at a speed up to 2 cm per second on a Molecular Electronics Corporation Monofab II continuous fabrication trough.

EXAMPLE 3

Introduction of Surface Hydroxyls on an L-B Film Using Alkaline Potassium Permanganate A dilute solution of analytical grade potassium permanganate (KMnO₄) (Mallinckrodt) was prepared at a concentration of 0.01M and its pH adjusted to pH=9 by the dropwise addition of aliquots of 0.1M sodium hydroxide (NaOH). The pH adjusted solution was allowed to cool to approximately 4° C. by placing it in a refrigerator. Previously cleaned and conditioned, chromium plated, soda lime glass slides, each 3"×3" (EMC Micromask LRG 306) and bearing the built-up L-B film, were immersed in the cold potassium permanganate solution for varying periods of time. Each slide was subsequently removed after its allotted time of reaction of 1, 3, 5, 10, and 30 minutes. The slides were then rinsed sequentially in deionized distilled water, followed by dilute HCL, then finally in deionized distilled water. The film bearing slides were then placed in a desiccator which was kept at room temperature and allowed to dry for no less than 48 hours. The contact angle made by water on the chemically treated surfaces and on untreated reference film was subsequently measured using a Rame Hart Contact Angle Goniometer. The contact angle of the untreated film was found to be 85°±5°. Table 1 shows the measured contact angles of the treated and untreated films as a function of treatment time in this reaction medium.

TABLE 1

Contact Angles of Water at the KNmO₄ Treated L-B film Surface

| Film | Contact Angle (Degrees) |
|---|---|
| Untreated | 85 |
| 1 minute | 18 |
| 3 minutes | 10 |
| 5 minutes | 10 |
| 10 minutes | 10 |

The reaction of the double bond terminated L-B film with the permanganate solution is limited to the outermost L-B layer and limited to the double bond at the terminus of that layer. This is evident from the absence of any color change associated with the diffracted and reflected light through the thin, built-up L-B film. These films, which are each about 930 A thin, appear blue when viewed in natural light. During film fabrication, the various natural colors of the visible spectrum emerge as the film thickness grows from its first monolayer through its 30th layer. The blue color, of varying intensities, appears for the 24th through 30th layer. The absence of an obvious color change confirms that no outer layers were removed. Examination of these chemically treated films by optical microscopy at X-400 magnification revealed no discernable morphological changes. This reaction introduces predominantly alcohols under these conditions and possibly some carboxylic acids as shown in the reaction scheme of FIG. 3.

EXAMPLE 4

Introduction of Surface Hydroxyls on an L-B Film Using Osmium Tetroxide

Dilute aqueous solutions of 0.02% osmium tetroxide was prepared by dilution of stock ampules of 0.2% aqueous osmium tetroxide solution (Polysciences). Previously cleaned and conditioned, chromium plated, soda lime glass slides, each 3"×3" (EMC Micromask LRG 306) and bearing the built-up L-B film, were immersed in the osmium tetroxide solution for varying periods of time at room temperature. Each slide was subsequently removed after its allotted time of reaction of 1, 3, 5, 10, and 30 minutes then rinsed profusely in deionized, distilled water. The films were then dried for at least 48 hours in a desiccator which was kept at room temperature. The contact angle made by water on the chemically treated surface and on untreated reference film was subsequently measured using a Rame Hart Contact Angle Goniometer. The contact angle at the chemically treated surface was found in all cases to be ca. 75 degrees while the untreated surface was measured at 85°±5°. In another sequence of experiments, the slides were transferred to and immersed in a stirred, dilute solution (0.01M) of aqueous sodium sulphite (Na$_2$SO$_3$) prior to the desiccatoin step. The films were submerged for a period of 1 minute, removed, then rinsed profusely in distilled, deionized water and dried at room temperature in a desiccator under pre-purifid argon for at least 48 hours. The contact angle of water measured on each of these films was in all cases less than 10 degrees. The reaction of osmium tetroxide with olefinic double bonds forms the osmate ester, which, on subsequent hydrolysis leaves the di-alcohols at the surface as shown in the reaction scheme of FIG. 4.

EXAMPLE 5

Introduction of Surface Carboxylic Acids on an L-B Film Using Acidic Potassium Permanganate A dilute solution of analytical grade potassium permanganate (KMnO$_4$) (Mallinckrodt) was prepared at room temperature at a concentration of 0.01M in 0.1 molar aqueous hydrochloric acid (HCl). Previously cleaned and conditioned, chromium plated, soda lime glass slides, each 3"×3" (EMC Micromask LRG 306) and bearing the built-up L-B film, were immersed in the potassium permanganate solution for varying periods of time. Each slide was subsequently removed after its allotted time of reaction of 1, 3, 5, 10, and 30 minutes. The slides were then rinsed sequentially in deionized distilled water, followed by dilute HCL, then finally in deionized, distilled water. The film bearing slides were then immersed in a room temperature solution of dilute NaOH (0.01 molar) for approximately 1 minute, removed, then rinsed profusely in deionized, distilled water. The film bearing slides were then placed in a desiccator, which was kept at room temperature, and allowed to dry for at least 48 hours. The contact angle made by water on the chemically treated surfaces and on untreated reference film was subsequently measured using a Rame Hart Contact Angle Gonimeter. The contact angle of the untreated film was found to be 85°±5°. Table 2 shows the measured contact angles of the treated and untreated films as a function of treatment times in this reaction medium.

TABLE 2

| Contact Angles of Water at the Acidified, KMnO$_4$ Treated L-B film Surface | |
|---|---|
| Film | Contact Angle (Degrees) |
| Untreated | 85 |
| 1 minute | 35 |
| 3 minutes | 20 |
| 5 minutes | 10 |
| 10 minutes | 10 |
| 30 minutes | about 0 |

The reaction of the double-bond-terminated L-B film with the permanganate solution is limited to the outermost L-B layer and limited to the double bond at the terminus of that layer. This is evident from the absence of any color change associated with the diffracted and reflected light through the thin, built-up L-B film. These films, which are each about 930 A thin, appear blue when viewed in natural light. During film fabrication, the various natural colors of the visible spectrum emerge as the film thickens from its first monolayer through its 30th layer. The blue color, of varying intensities, appears for the 24th through 30th layer. The absence of an obvious color change confirms that no outer layers were removed. Examination of these chemically treated films by optical microscopy at X-400 magnification revealed no discernable, gross morphological changes. The permanganate reaction under these conditions is known to introduce predominantly carboxylic acids and possibly some residual alcohols are retained as shown in the reaction scheme of FIG. 5.

EXAMPLE 6

L-B Film Complexes by Deposition of L-B Film Monolayers onto a Chemically Modified L-B Film Surface Microscope slides, each 3"×3" and bearing the surface modified, built-up L-B film, surface modified according to Example 5, were dipped through the air/water interface at 10 mm/sec through a Langmuir monolayer film of octadecyl amine held at a film pressure of 20 mN/m. The slide was withdrawn at 0.2 mm/sec$^{-1}$ to yield the built-up supra-macromolecular structure shown in FIG. 6. The film bearing slides were then placed in a desiccator kept at room temperature and allowed to dry for approximately 48 hours. The contact angle made by water on the newly formed L-B film surface and on undipped reference film was measured using a Rame Hart Contact Angle Goniometer. The contact angle of the undipped film was found to be 12°±2°. The newly formed supra-macromolecular complex was found to have a contact angle of 82°±7°. The resulting film surface is again hydrophobic with the final layer consisting of a tail-to-head arrangement of a tail group, converted by surface chemical modification to resemble a head group in character, and an amine head group.

EXAMPLE 7

Immobilization of the Enzyme Cofactor-FAD on a Chemically Modified L-B Film Surface The surface carboxylic acid functionalities produced by the above procedures (according to Example 5)

were made to react with the water-soluble carbodiimide, 1-ethly-3(3-dimethylaminopropyl)carbodiimide hydrochloride (Pierce Chemicals), to yield the surface confined isourea product (Mayawaki, O., and Wingard, Jr., L. B., *Biochemica and Biophysica Acta,* 838,60 (1985). The chemically modified slides were immersed in 1 mg/ml aqueous, room temperature solutions of the carbodiimide for about 4 hours. The resulting isourea surface was then rinsed thoroughly in deionized, distilled water and immersed in a cold, aqueous solution of the disodium salt of high-purity FAD (Boehriger-Mannheim Biochemicals) and incubated overnight at 5° C. in a refrigerator. This reaction yielded the FAD derivatized Langmuir-Blodgett film and resulted in FAD coupling to the built-up L-B film via the primary amine of the adenine base of FAD as shown in FIG. 7. However, the possibility of linking reactions occurring through the hydroxyl functional group has not been discounted.

EXAMPLE 8

Immobilization of the Enzyme Glucose Oxidase On a Chemically Modified L-B Film Surface Microscope slides (each 3"×3") and bearing the surface modified, built-up L-B film (surface modified according to Example 3) were immersed in a saturated solution of p-benzoquinone which was previously prepared in aqueous 1% isopropyl alcohol. After approximately 30 minutes of immersion, the slides were removed, rinsed in deionized, distilled water, then immediately transferred to a cold, pH 7.2, phosphate-buffered saline solution of glucose oxidase (Type VII-S; EC 1.1.3.4 from *Aspergillus niger;* 129,000 units of activity per gram of solid.) The slides were then incubated overnight in the glucose oxidase solution in a refrigerator at about 5° C. Benzoquinone is well known to cause chemical activation of hydroxyl containing surfaces (J. Brandt, L. O. Anderson, and J. Porath, *Biochim. Biophys. Acta,* 386; 196(1976)) through formation of the hydroxy quinone. The surface confined hydroxy quinone then acts as an effective linking agent between the activated surface and enzyme molecules (K. Narasimhan and L. B. Wingard, Jr., *Enzyme Microb. Technol.,* 7;283(1985)). Following overnight incubation, the slides were removed and tested for immobilized enzyme activity using the method described by L. B. Wingard, Jr., L. A. Cantin, and J. F. Castner in *Biochim. and Biophys. Acta,* 748:21(1983)). Blank slides were found to have around 0.4 munits of activity per square centimeter while functionalized and activated slides were found to have around 50 munits of activity per square centimeter, thereby showing clear activation and immobilization of the enzyme.

INDUSTRIAL APPLICABILITY

The invention described herein relates to the surface chemical modification and surface chemical functionalization or derivatization of built-up L-B films and the processes for the introduction of chemically active, specific and catalytic overlayers. This is achieved through the surface chemical modification of hydrophobic L-B film surfaces to reactive functionalities capable of specific covalent bonding and chemical association. Such new films have technological utility owing to improved wettability when in contact with aqueous environments. This modification allows for the direct chemical covalent bonding of bioactive entities such as enzymes, antibodies, cofactors, hormones, haptens, and the like. Alternatively, this chemical modification allows the immobilization of chemical entities which can impart optoactive, thermoactive, electroactive, redox active and mechanically active properties to the film surface.

EQUIVALENTS

Those skilled in the art will recognize, or be able to ascertain using no more than routine experimentation, many equivalents to the specific embodiments of the invention described herein. Such equivalents are intended to be encompassed in the following claims.

I claim:

1. A process for chemically modifying a hydrophobic surface of a Langmuir-Blodgett film so as to make said surface hydrophilic, said process comprising:
   a. providing a Langmuir-Blodgett film having a hydrophobic surface of omega unsaturated covalent bonds formed from an amphiphilic, bifunctional surface active material having a hydrophobic tail group bearing an omega terminus of double or triple bonded unsaturation; and
   b. exposing the hydrophobic surface of the Langmuir-Blodgett film to a reagent which reacts with the surface of the Langmuir-Blodgett film for a time sufficient so as to oxidize said omega unsaturated covalent bonds to provide hydrophilic groups on said surface thus providing a hydrophilic surface on the Langmuir-Blodgett film.

2. The process of claim 1 wherein the amphiphilic material is selected from the group consisting of bifunctional, surface active molecules having both ionizable and non-ionizable head groups.

3. The process of claim 2 wherein the amphiphilic material is selected from the group consisting of fatty acids, phospholipids, porphyrins and their derivatives.

4. The process of claim 3 wherein the fatty acids are selected from the group consisting of arachidic acid, stearic acid, heptadecanoic acid, hexadeconic acid, and their derivatives.

5. The process of claim 3 wherein the porphyrins are selected from the group consisting of phthalocyanine, merocyanine and their derivatives.

6. The process of claim 1 wherein the amphiphilic material is selected from the group consisting of omega-tricosenoylamide and omega-tricosenoic acid.

7. The process of claim 1 wherein the reagent which reacts with the surface provides a surface having a hydroxyl functionality.

8. The process of claim 7 wherein the reagent which reacts with the surface is an aqueous reagent selected from the group consisting of alkaline potassium permanganate, potassium dichromate and osmium tetroxide.

9. The process of claim 1 wherein the reagent which reacts with the surface provides a surface having a carboxylic acid functionality.

10. The process of claim 9 wherein the reagent which reacts with the surface is an aqueous reagent comprising acidic potassium permanganate.

11. The process of claim 1 comprising the additional step of exposing the surface of the Langmuir-Blodgett film to additional chemical reagents subsequent to providing the hydrophilic groups, said additional reagents being reactive with the hydrophilic groups on the surface of the Langmuir-Blodgett film, and said exposure being for a time sufficient to immobilize the additional chemical reagents on the surface of the Langmuir-Blodgett film.

12. process of claim 11 wherein the additional chemical reagent is selected from the group consisting of biologically active reagents.

13. The process of claim 12 wherein the biologically active reagents are selected from the group consisting of enzymes, enzyme conjugates, cofactors, antigens, antibodies, RNA, DNA, hormones, enzyme inhibitors and enzyme substrates.

14. The process of claim 13 wherein the biologically active reagent comprises glucose oxidase.

15. The process of claim 13 wherein the biologically active reagent comprises flavin adenine dinucleotide.

16. The process of claim 1 comprising the additional step of depositing a subsequent Langmuir-Blodgett film upon the Langmuir-Blodgett film containing hydrophilic groups.

17. The process of claim 16 wherein the subsequent Langmuir-Blodgett film is of a composition different from that of the Langmuir-Blodgett film containing hydrophilic groups.

18. The process of claim 16 wherein the subsequent Langmuir-Blodgett film comprises built-up monolayers of amphiphilic material.

19. The process of claim 18 wherein the amphiphilic material is selected from the group consisting of bifunctional, surface active molecules having both ionizable and non-ionizable head groups.

20. The process of claim 19 wherein the amphiphilic material is selected from the group consisting of fatty acids, phospholipids, porphyrins and their derivatives.

21. The process of claim 20 wherein the fatty acids are selected from the group consisting of arachidic acid, stearic acid, heptadecanoic acid, hexadeconic acid, and their derivatives.

22. The process of claim 20 wherein the porphyrins are selected from the group consisting of phthalocyanine, merocyanine and their derivatives.

23. The process of claim 18 wherein the amphiphilic material is selected from the group consisting of bifunctional, surface active molecules having hydrophobic tail groups bearing an omega terminus of double or triple bonded unsaturation.

24. The process of claim 23 wherein the amphiphilic material is selected from the group consisting of omega-tricosenoylamide and omega-tricosenoic acid.

25. The process of claim 3 wherein the phospholipids are selected from the group consisting of phosphatidylcholine, bis-[12-(methacryloyloxy)dodecanoyl]-L-phosphatidylcholine and their derivatives.

26. The process of claim 20 wherein the phospholipids are selected from the group consisting of phsophatidylcholine, bis-[12-(methacryloyloxy)-dodecanoyl]-L-phosphatidylcholine and their derivatives.

27. A Langmuir-Blodgett film having a hydrophilic surface prepared by the process of claim 1.

28. A process for preparing a Langmuir-Blodgett film/supra-molecular complex, said process comprising:
  a. providing a Langmuir-Blodgett film having a hydrophobic surface of omega unsaturated covalent bonds formed from an amphiphilic, bifunctional surface active material having a hydrophobic tail group bearing an omega terminus of double or triple bonded unsaturation;
  b. exposing the hydrophobic surface of the Langmuir-Blodgett film to a reagent which reacts with the surface of the Langmuir-Blodgett film for a time sufficient so as to oxidize said omega unsaturated covalent bonds on said surface so as to form hydroxyl or carboxylic acid groups thus providing a hydrophilic surface on the Langmuir-Blodgett film; and
  c. exposing the hydrophilic surface of the Langmuir-Blodgett film to a chemical reagent that is active to the surface of the film for a time sufficient to provide immobilization of the chemical reagent on the film surface, to thereby result in the creation of a Langmuir-Blodgett film/supra-molecular complex.

29. A Langmuir-Blodgett film/supra-molecular complex prepared by the following steps:
  a. providing a Langmuir-Blodgett film having a hydrophobic surface of omega unsaturated covalent bonds formed from an amphiphilic, bifunctional surface active material having a hydrophobic tail group bearing an omega terminus of double or triple bonded unsaturation;
  b. exposing the hydrophobic surface of said Langmuir-Blodgett film to reagents which react with the surface of the Langmuir-Blodgett film for a time sufficient so as to oxidize said omega unsaturated covalent bonds so as to form hydroxyl or carboxylic acid groups on said surface thus providing a hydrophilic surface on the Langmuir-Blodgett film; and
  c. exposing the hydrophilic surface of the Langmuir-Blodgett film to an additional chemical reagent that is active to the surface of the film for a time sufficient to provide immobilization of the additional chemical reagent on the film surface to result in a Langmuir-Blodgett film/supra-molecular complex.

30. The complex of claim 29 wherein built-up monolayers of amphiphilic material are formed on the Langmuir-Blodgett film having a hydrophilic surface.

31. The complex of claim 30 wherein the amphiphilic material is selected from the group consisting of bifunctional, surface active molecules having both ionizable and non-ionizable head groups.

32. The complex of claim 31 wherein the amphiphilic material is selected from the group consisting of fatty acids, phospholipids, porphyrins and their derivatives.

33. The complex of claim 32 wherein the fatty acids are selected from the group consisting of arachidic acid, stearic acid, heptadecanoic acid, hexadeconic acid, and their derivatives.

34. The complex of claim 32 wherein the porphyrins are selected from the group consisting of phthalocyanine, merocyanine and their derivatives.

35. The complex of claim 30 wherein the amphiphilic material is selected from the group consisting of bifunctional, surface active molecules having hydrophobic tail groups bearing an omega terminus of double or triple bonded unsaturation.

36. The complex of claim 30 wherein the amphiphilic material is selected from the group consisting of omega-tricosenoylamide and omega-tricosenoic acid.

37. The complex of claim 29 wherein the reagent which reacts with the surface provides a surface having a hydroxyl functionality.

38. The complex of claim 31 wherein the reagent which reacts with the surface provides a surface having a carboxyl functionality.

39. The complex of claim 29 wherein the additional chemical reagent is selected from the group consisting of biologically active reagents.

40. The complex of claim 39 wherein the biologically active reagents are selected from the group consisting of enzymes, cofactors, antigens, antibodies, enzyme conjugates, RNA, DNA, hormones, enzyme inhibitors and enzyme substrates.

41. The complex of claim 40 wherein the biologically active reagent comprises glucose oxidase.

42. The complex of claim 40 wherein the biologically active reagent comprises flavin adenine dinucleotide.

43. The complex of claim 29 wherein the additional chemical reagent comprises a subsequent Langmuir-Blodgett film.

44. The complex of claim 43 wherein the subsequent Langmuir-Blodgett film is of a composition different from that of the precursor Langmuir-Blodgett film.

45. The complex of claim 44 wherein the subsequent Langmuir-Blodgett film comprises octadecylamine.

46. The complex of claim 32 wherein the phospholipids are selected from the group consisting of phsophatidylcholine, bis-[12-(methacryloyloxy)-dodecanoyl]-L-phosphatidylcholine and their derivatives.

47. A process for chemically modifying a hydrophobic surface of a Langmuir-Blodgett film so as to provide a hydroxyl or carboxylic acid functionality on said surface, said process comprising:
  a. providing a Langmuir-Blodgett film having a hydrophobic surface of omega unsaturated covalent bonds formed from an amphiphilic, bifunctional surface active material having a hydrophobic tail group bearing an omega terminus of double or triple bonded unsaturation; and,
  b. exposing the hydrophobic surface of the Langmuir-Blodgett film to a reagent which reacts with the surface of the Langmuir-Blodgett film for a time sufficient so as to oxidize said omega unsaturated covalent bonds on the surface thus providing a carboxylic acid or hydroxyl functionality on the Langmuir-Blodgett film.

48. A process for chemically modifying a hydrophobic surface of a Langmuir-Blodgett film so as to make said surface hydrophilic, said process comprising:
  a. providing a Langmuir-Blodgett film having a hydrophobic surface of omega unsaturated covalent bonds, said Langmuir-Blodgett film comprising built-up monolayers of amphilphilic material wherein the amphiphilic material is selected from the group consisting of omega-tricosenoylamide and omega-tricosenoic acid; and
  b. exposing the hydrophobic surface of the Langmuir-Blodgett film to a regent which reacts with the surface of the Langmuir-Blodgett film for a time sufficient so as to oxidize said omega unsaturated covalent bonds to provide hydrophilic groups on said surface thus providing a hydrophilic surface on the Langmuir-Blodgett film.

* * * * *